(12) United States Patent
Okamoto

(10) Patent No.: US 11,432,710 B2
(45) Date of Patent: Sep. 6, 2022

(54) EXTERNAL MECHANISM FOR ENDOSCOPE AND ENDOSCOPE SYSTEM

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 87 days.

(21) Appl. No.: 16/901,262

(22) Filed: Jun. 15, 2020

(65) Prior Publication Data

US 2020/0367725 A1  Nov. 26, 2020

Related U.S. Application Data

(63) Continuation of application No. PCT/JP2018/045836, filed on Dec. 13, 2018.

(30) Foreign Application Priority Data

Dec. 18, 2017 (JP) .............................. JP2017-241491

(51) Int. Cl.
*A61B 1/005* (2006.01)
*A61B 1/00* (2006.01)

(52) U.S. Cl.
CPC ........ *A61B 1/0052* (2013.01); *A61B 1/00006* (2013.01); *A61B 1/00016* (2013.01); *A61B 1/0016* (2013.01)

(58) Field of Classification Search
CPC ......... F16H 57/031; F16H 2057/02039; A61B 1/0052; A61B 1/005; A61B 1/0051;
(Continued)

(56) References Cited

U.S. PATENT DOCUMENTS

2010/0268031 A1    10/2010  Koyama
2014/0371534 A1*   12/2014  Okamoto ........... A61B 1/00066
                                                        600/118
2016/0296103 A1*   10/2016  Gotz .................. A61B 1/00066

FOREIGN PATENT DOCUMENTS

JP     H02-055907 U    4/1990
JP     H05-300873 A   11/1993
(Continued)

OTHER PUBLICATIONS

English translation of Takahashi (JPH05300873A), foreign copy provided by the Applicant, English translation through Espacenet. (Year: 1993).*

(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An external mechanism for endoscope includes a wheel engaged with a second bending operation up and down knob of a second bending operation apparatus provided in an operation portion of an endoscope, a motor configured to generate driving force for rotating the wheel, an operation switch for outputting a driving control signal to the motor, a container case containing the wheel and the motor, a case attachment and detachment fixation member with which the container case can be attached to and detached from the operation portion, a switch case attached to the container case and configured to be able to turn between a first position covering a part of the operation portion and a second position away from the first position, and a dummy switch provided in the switch case and configured to operate a remote switch arranged in the operation portion in the first position via the switch case.

4 Claims, 12 Drawing Sheets

(58) Field of Classification Search
CPC ............ A61B 1/00131; A61B 1/00133; A61B 1/00147; A61B 1/0016; A61B 34/30; A61B 2034/301–303; A61B 34/32; A61B 34/35; A61B 34/70–72
USPC ......... 600/146, 139, 141, 147–148, 118, 152
See application file for complete search history.

(56) References Cited

FOREIGN PATENT DOCUMENTS

| | | |
|---|---|---|
| JP | H11-032977 A | 2/1999 |
| JP | 2008-048788 A | 3/2008 |
| WO | WO 2010/047223 A1 | 4/2010 |
| WO | WO 2012/063880 A1 | 5/2012 |

OTHER PUBLICATIONS

International Search Report dated Mar. 26, 2019 issued in PCT/JP2018/045836.

* cited by examiner

EXTERNAL MECHANISM FOR ENDOSCOPE AND ENDOSCOPE SYSTEM

CROSS REFERENCE TO RELATED APPLICATION

This application is a continuation application of PCT/JP2018/045836 filed on Dec. 13, 2018 and claims benefit of Japanese Application No. 2017-241491 filed in Japan on Dec. 18, 2017, the entire contents of which are incorporated herein by this reference.

BACKGROUND OF THE INVENTION

1. Field of the Invention

The present invention relates to an external mechanism for endoscope which can be attached to and detached from a bending operation knob of an endoscope and turns the knob by driving force of a motor unit and bends a bending portion provided in an insertion portion, and an endoscope system.

2. Description of the Related Art

An endoscope is used in a medical field, an industrial field, and the like. The endoscope includes a bending portion in an elongated insertion portion that is inserted into a subject.

Japanese Patent Application Laid-Open Publication No. 2008-48788 illustrates an endoscope including a first bending portion and a second bending portion arranged in parallel on a distal end side of an elongated insertion portion in an extending direction of the insertion portion, and having a main bending operation apparatus and a sub bending operation apparatus provided in an operation portion located on a proximal end side of the insertion portion. In the aforementioned endoscope, an operation knob of the main bending operation apparatus is turned and operated to perform a bending operation of the first bending portion, and an operation knob of the sub bending operation apparatus is turned and operated to perform a bending operation of the second bending portion.

Therefore, when a user bends the first bending portion or the second bending portion by independently turning and operating each of the operation knobs, the insertion portion can be smoothly inserted into a complicatedly winding lumen, and it is possible to easily direct a built-in observation optical system on the distal end side of the insertion portion in a desired direction.

In the operation portion illustrated in Japanese Patent Application Laid-Open Publication No. 2008-48788, the sub bending operation apparatus is provided away from the main bending operation apparatus on a proximal end side of the operation portion on an opposite side to the insertion portion from the main bending operation apparatus. For this reason, it is difficult for the user to smoothly switch a turning operation of the main bending operation apparatus and a turning operation of the sub bending operation apparatus by a finger of a hand that grasps the operation portion. When the knob of the bending operation apparatus is turned and operated, a large load is applied to the finger of the user.

In view of this point, an external electrically-driven bending mechanism is devised which can be attached to and detached from an operation portion and is configured to turn a sub bending operation apparatus in an attached state by driving force of a driving source such as a motor.

In a general endoscope, for example, a remote operation switch or the like for acquiring and recording still images is arranged. In the above-described external electrically-driven bending mechanism, the remote operation switch needs to be operably exposed in the attached state.

SUMMARY OF THE INVENTION

An external mechanism for endoscope according to one aspect of the present invention includes: a wheel configured to be engaged with an operation knob of a bending operation apparatus provided in an operation portion of an endoscope; a driving source configured to generate driving force for rotating the wheel; an operation switch configured to output a driving control signal for the driving source; a container case that contains the wheel and the driving source; an attachment and detachment fixation member with which the container case can be attached to and detached from the operation portion; a turning member turnably attached to the container case, and configured to be able to turn between a first position that covers a part of the operation portion of the endoscope and a second position away from the first position; and an operation member provided in the turning member and configured to operate an endoscope-side switch via the turning member when the turning member is in the first position, the endoscope-side switch being arranged in a part of the operation portion of the endoscope.

An endoscope system according to another aspect of the present invention includes: an endoscope; and an external mechanism that can be attached to and detached from an operation portion of the endoscope, wherein the endoscope includes a bending knob provided in the operation portion and configured to bend a bending portion of an insertion portion when the bending knob is turned; and an endoscope operation control switch arranged in a part of the operation portion and configured to execute a predetermined operation in the endoscope by being operated, and the external mechanism includes a wheel configured to be engaged with the bending knob to turn the bending knob, a driving source configured to generate driving force for rotating the wheel, an operation switch configured to output a driving control signal for the driving source, a container case that contains the wheel and the driving source, an attachment and detachment fixation member with which the container case can be attached to and detached from the operation portion, a turning member turnably attached to the container case, and configured to be able to turn between a first position that covers a part of the operation portion of the endoscope and a second position away from the first position; and an operation member provided in the turning member and configured to operate the endoscope operation control switch via the turning member when the turning member is in the first position.

DETAILED DESCRIPTION OF THE PREFERRED EMBODIMENT

Hereinafter, an embodiment of the present invention will be described with reference to the drawings.

Note that in each of the drawings used for the following description, to set approximate sizes of respective components to be recognizable on the drawings, scale sizes of some components are varied for the respective components. In other words, the present invention is not limited only to the number of components, shapes of the components, a ratio of the sizes of the components, and a relative positional relationship between the respective components illustrated in these drawings.

A configuration of an endoscope will be described with reference to FIG. 1.

Figure 1:
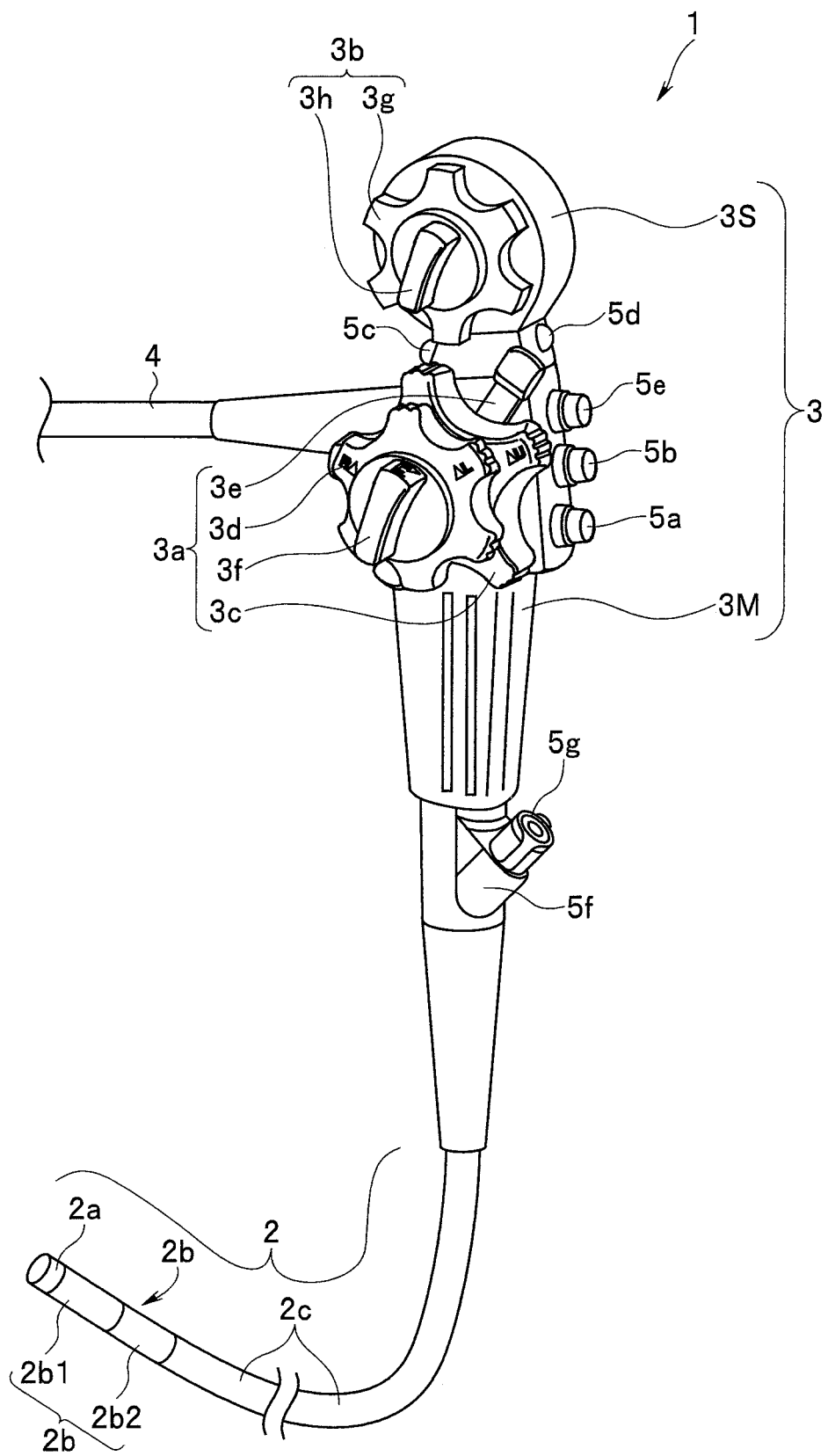
FIG. 1 is a drawing for describing a configuration example of an endoscope.

An endoscope 1 illustrated in FIG. 1 includes an elongated insertion portion 2, an operation portion 3 doubling as a grasping portion, and a universal cord 4. In the insertion portion 2, a distal end portion 2a, a bending portion 2b, and a lengthy flexible tube portion 2c having flexibility are continuously disposed from a distal end side in the stated order.

According to the present embodiment, the bending portion 2b has a first bending portion 2b1 and a second bending portion 2b2. The first bending portion 2b1 is provided on a distal end side of the insertion portion 2. The second bending portion 2b2 is disposed to be continuous to a proximal end portion of the first bending portion 2b1 via a linking portion (not illustrated). The first bending portion 2b1 is bendable, for example, in up-down and left-right directions. In contrast, the second bending portion 2b2 is bendable in the up-down direction.

The operation portion 3 has a first bending operation apparatus 3a and a second bending operation apparatus 3b. According to the present embodiment, the operation portion 3 has a main operation portion 3M which doubles as a grasping portion and in which the first bending operation apparatus 3a is provided, and a sub operation portion 3S which is provided on a proximal end side of the main operation portion 3M and in which the second bending operation apparatus 3b is provided. The second bending operation apparatus 3b is provided on an operation portion proximal end side corresponding to an opposite side to the insertion portion 2 away from the first bending operation apparatus 3a.

The first bending operation apparatus 3a has a first bending portion up and down operation knob (hereinafter, abbreviated as a first bending up and down knob) 3c and a first bending portion left and right operation knob (hereinafter, abbreviated as a first bending left and right knob) 3d as a bending operation knob, a first bending portion up and down direction fixation lever (hereinafter, abbreviated as a first bending up and down fixation lever) 3e, and a first bending portion left and right direction fixation finger grip (hereinafter, abbreviated as a first bending left and right fixation finger grip) 3f.

The second bending operation apparatus 3b has a second bending portion up and down operation knob (hereinafter, abbreviated as a second bending up and down knob) 3g serving as a bending operation knob, and a second bending portion up and down direction fixation lever (hereinafter, abbreviated as a second bending up and down fixation lever) 3h.

The first bending up and down knob 3c is turned when bending operation of the first bending portion 2b1 is performed in the up and down direction. The first bending left and right knob 3d is turned when bending operation of the first bending portion 2b1 is performed in the left and right direction. The first bending up and down fixation lever 3e can be switched between a free position and a fixed position. The first bending left and right fixation finger grip 3f can be switched between a free position and a fixed position.

When the first bending up and down fixation lever 3e is in the free position, the turning operation of the first bending up and down knob 3c can be performed. At this time, the first bending portion 2b1 is in a state of being bent in an up direction or a down direction along with the turning operation of the first bending up and down knob 3c. When the first bending left and right fixation finger grip 3f is in the free position, the turning operation of the first bending left and right knob 3*d* can be performed. At this time, the first bending portion 2*b*1 is in a state of being bent in a left direction or a right direction along with the turning operation of the first bending left and right knob 3*d*.

In contrast, when the first bending up and down fixation lever 3*e* is switched to the fixed position, the turning of the first bending up and down knob 3*c* is restricted. As a result, the bending state of the first bending portion 2*b*1 in the up and down direction is held in the state at the time of the switching. Similarly, when the first bending left and right fixation finger grip 3*f* is switched to the fixed position, the turning of the first bending left and right knob 3*d* is restricted. As a result, the bending state of the first bending portion 2*b*1 in the left and right direction is held in the state at the time of the switching.

The second bending up and down knob 3*g* is turned when bending operation of the second bending portion 2*b*2 is performed in the up and down direction. The second bending up and down fixation lever 3*h* can be switched between a free position and a fixed position.

When the second bending up and down fixation lever 3*h* is in the free position, the turning operation of the second bending up and down knob 3*g* can be performed. At this time, the second bending portion 2*b*2 is in a state of being bent in an up direction or a down direction along with the turning operation of the second bending up and down knob 3*g*. In contrast, when the second bending up and down fixation lever 3*h* is switched to the fixed position, the turning of the second bending up and down knob 3*g* is restricted. As a result, the bending state of the second bending portion 2*b*2 in the up and down direction is held in the state at the time of the switching.

Note that reference sign 5*a* denotes an air/water feeding button, reference sign 5*b* denotes a suction operation button, reference signs 5*c*, 5*d*, and 5*e* denote a remote switch, reference sign 5*f* denotes a treatment instrument insertion opening, and reference sign 5*g* denotes a forceps plug. The remote switch is a switch configured to perform stopping or recording of an endoscope image displayed on a screen of a display device (not illustrated), enlargement of an image, switching of illumination light, and the like, and an optimal function is allocated to each switch.

Figure 2A:
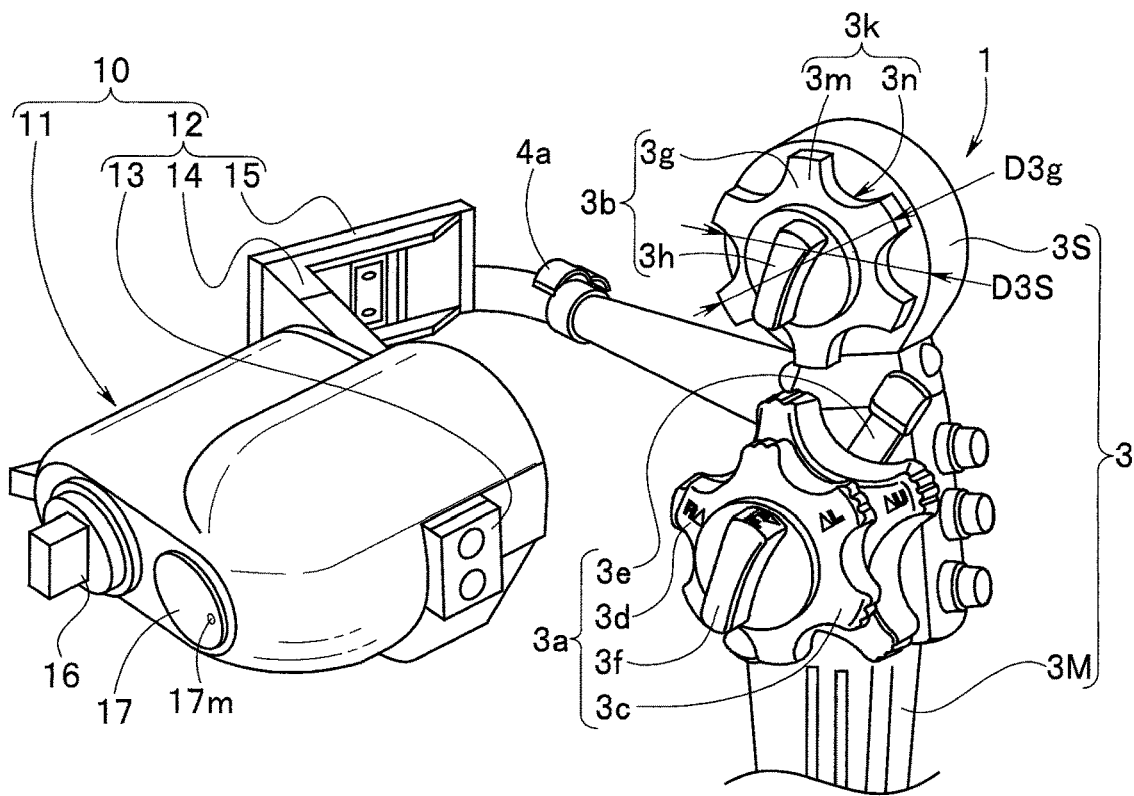
FIG. 2A is a drawing for describing a relationship between a sub operation portion serving as an operation portion of the endoscope and an external mechanism for endoscope.

Reference sign 10 in FIG. 2A denotes an external mechanism for endoscope. The external mechanism 10 for endoscope can be attached to and detached from the second bending up and down knob 3*g* provided in the sub operation portion 3S. The external mechanism 10 for endoscope is an assisting mechanism portion attached to the second bending up and down knob 3*g* and configured to turn the second bending up and down knob 3*g* by driving force of a motor (see reference sign 32 in FIG. 4B which will be described below) which will be described below.

Reference sign 11 denotes a container case, and reference sign 12 denotes a case attachment and detachment fixation portion (hereinafter, described as a case attachment and detachment portion). The case attachment and detachment portion 12 includes a locking portion 13, a hinge portion 14, and a locking claw portion 15.

The locking portion 13 is fixedly provided in a predetermined position of the container case 11. The hinge portion 14 is substantially L-shaped, and one end portion is turnably disposed in a predetermined position of the container case 11. The locking claw portion 15 is provided in the other end portion of the L-shaped hinge portion 14. When the hinge portion 14 fixes the locking claw portion 15 to be engaged with the locking portion 13, a turning state is restricted. Reference sign 16 denotes a switching finger grip, and reference sign 17 denotes a bending state display portion that includes a rotation index 17*m*.

Figure 2B:
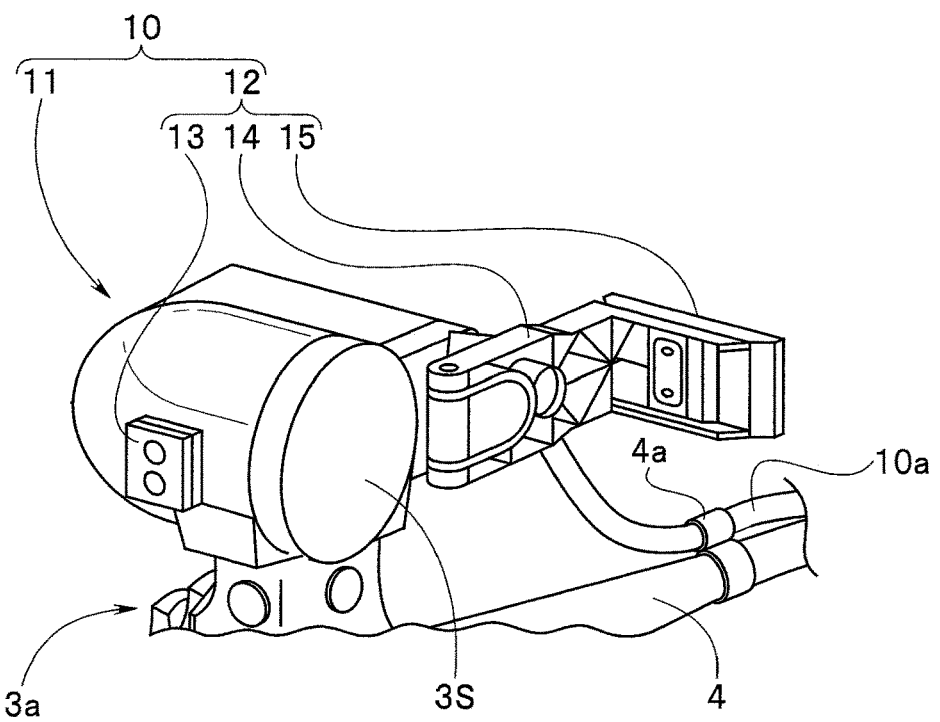
FIG. 2B is a drawing for describing a state where the external mechanism for endoscope is arranged in the sub operation portion.

Reference sign 4*a* denotes a cable mount. As illustrated in FIG. 2B, one or a plurality of the cable mounts 4*a* are provided in desired positions of the universal cord 4, to which an electric cable 10*e* is to be attached.

Figure 2C:
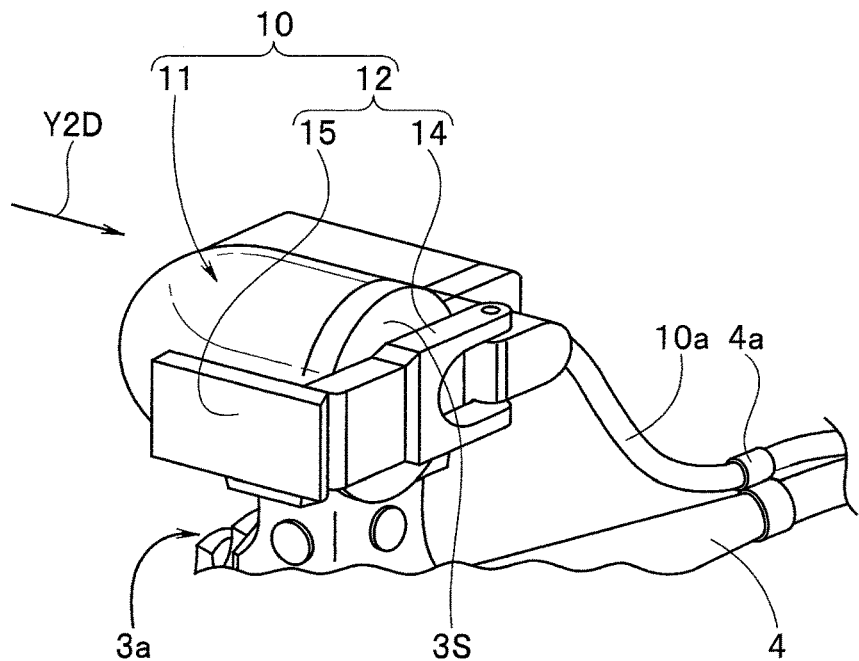
FIG. 2C is a drawing for illustrating the external mechanism for endoscope that is attached and fixed to the sub operation portion.
Figure 2D:
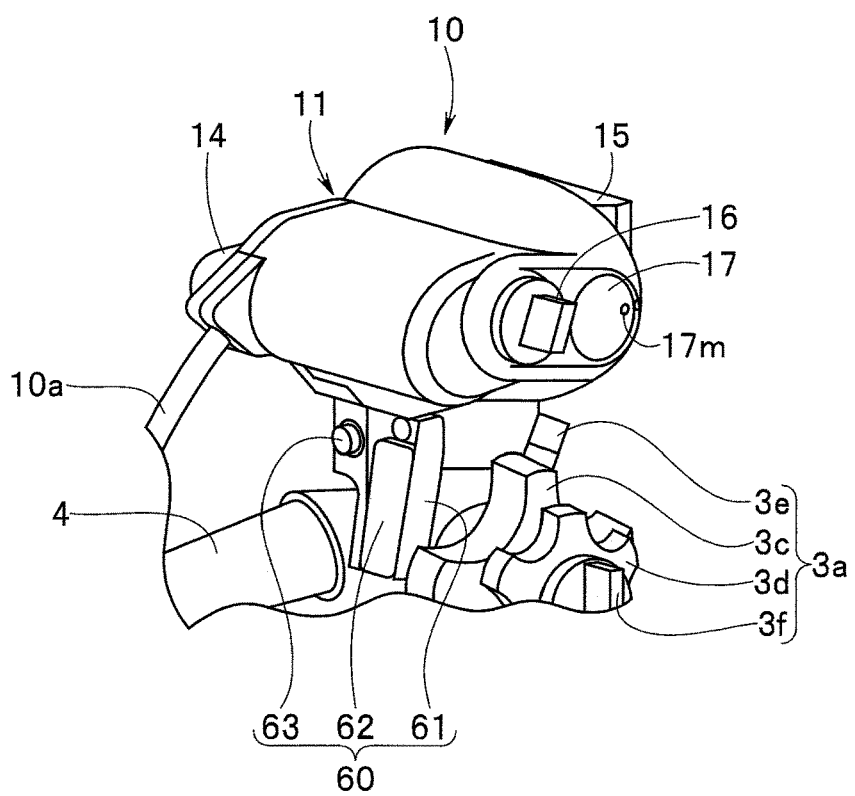
FIG. 2D is a view of the sub operation portion of FIG. 2C as viewed from an arrow 2D side.

In a state where the container case 11 is disposed on the sub operation portion 3S so as to cover the second bending up and down knob 3*g* as illustrated in FIG. 2B, the external mechanism 10 for endoscope is integrally attached to the sub operation portion 3S by causing the locking claw portion 15 to engage with and to be fixed to the locking portion 13 by rotating the hinge portion 14, with one end portion side of the hinge portion 14 as a fulcrum as illustrated in FIG. 2C and FIG. 2D.

Note that reference sign 60 in FIG. 2D denotes an operation switch, reference sign 61 denotes a switch case, reference sign 62 denotes an operator, and reference sign 63 denotes a dummy switch.

A configuration of the external mechanism 10 for endoscope will be described.

Figure 3:
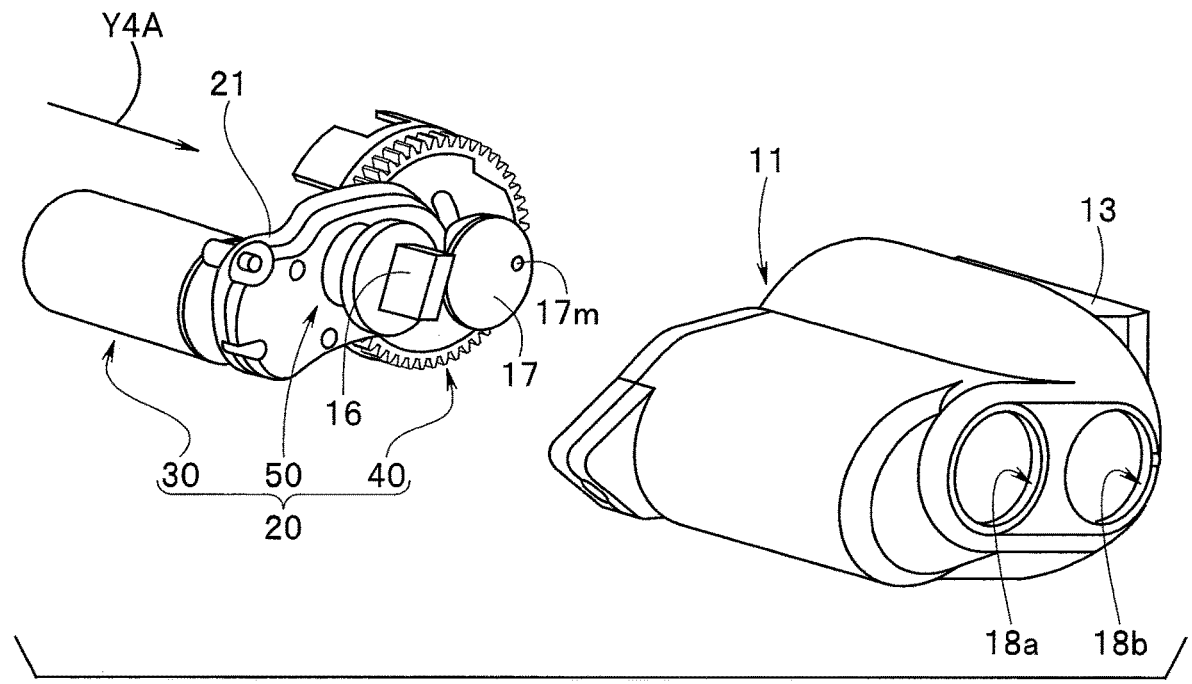
FIG. 3 is a drawing for describing a relationship between a container case of the external mechanism for endoscope and a knob rotation mechanism contained in the container case.

As illustrated in FIG. 3, the container case 11 of the external mechanism 10 for endoscope has a case internal space, and a knob rotation mechanism 20 is contained in the case internal space. The container case 11 is provided with a first through-hole 18*a* in which the switching finger grip 16 is to be disposed, and a second through-hole 18*b* in which the bending state display portion 17 is to be disposed. The through-holes 18*a* and 18*b* connect the case internal space to the outside.

The knob rotation mechanism 20 will be described with reference to FIG. 3, FIG. 4A, and FIG. 4B.

As illustrated in FIG. 3, the knob rotation mechanism 20 mainly includes a motor portion 30, a knob rotation portion 40, and a transmission portion 50. Reference sign 21 illustrated in FIG. 3 to FIG. 4B denotes a rotation mechanism main body that serves as an attachment member.

Figure 4A:
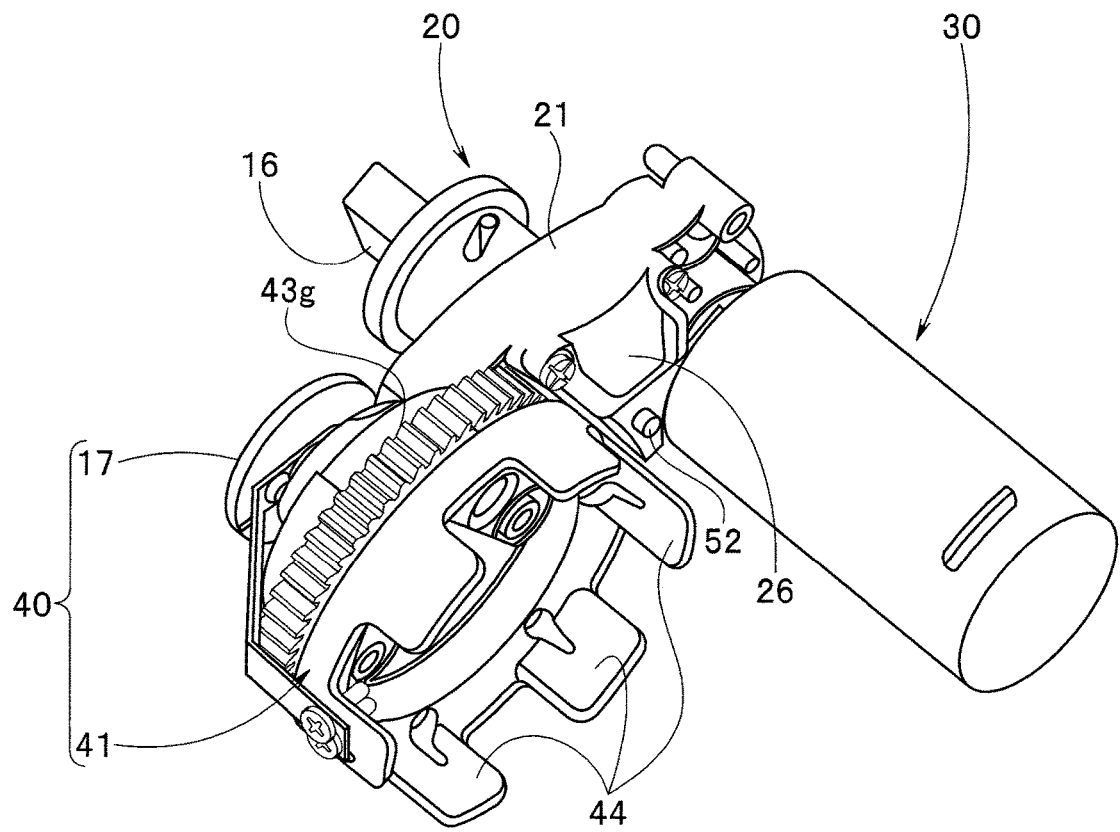
FIG. 4A is a view of the knob rotation mechanism as viewed in an arrow Y4A direction of FIG. 3.
Figure 4B:
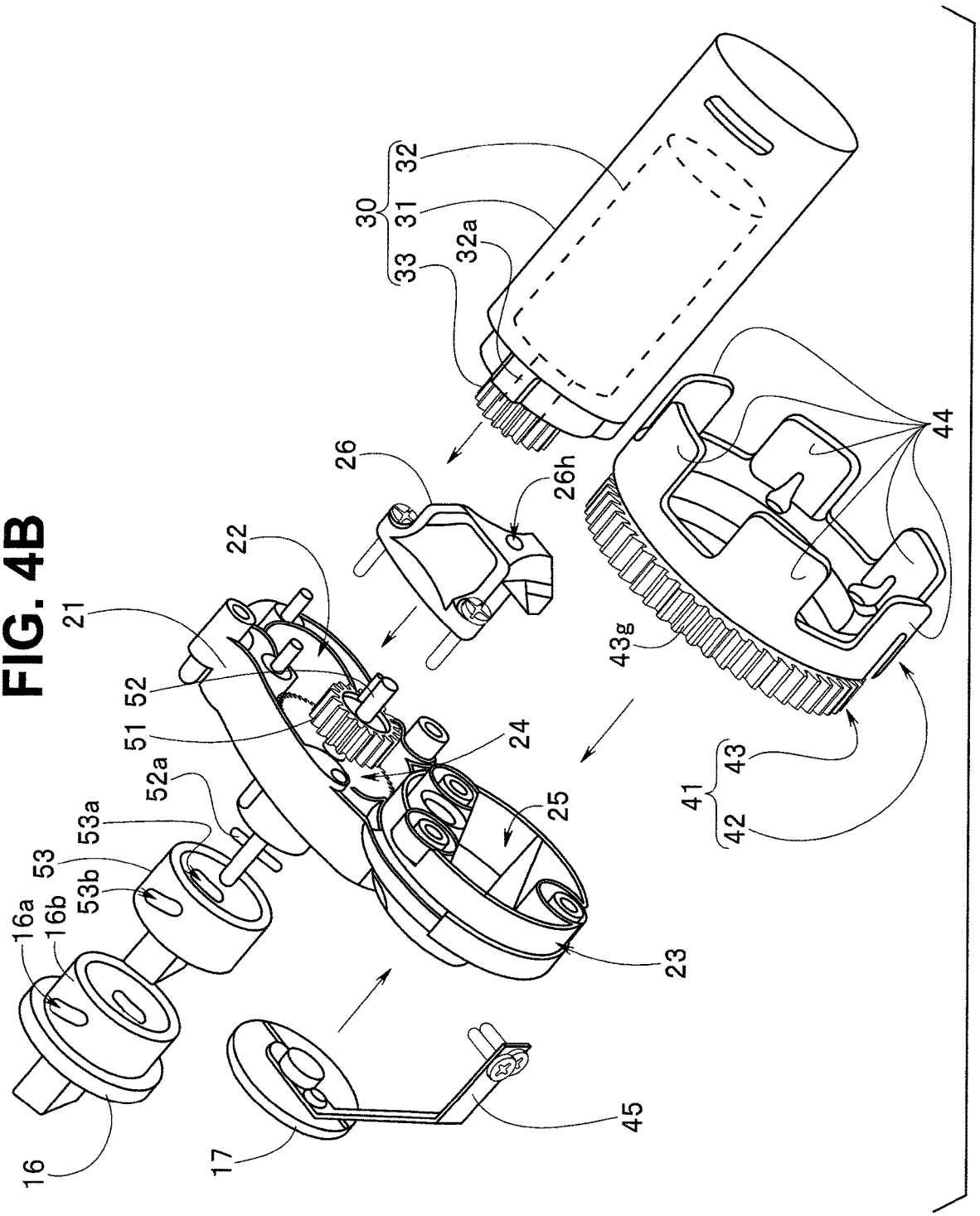
FIG. 4B is an exploded perspective view of an outline of a configuration of the knob rotation mechanism.

As illustrated in FIG. 4B, in the rotation mechanism main body 21, a motor attachment portion 22, a wheel attachment portion 23, a switching gear attachment portion 24, and the like are respectively provided in predetermined positions.

Reference sign 25 denotes a concave portion for lever corresponding to a hole formed to have such an external shape and a depth that the second bending up and down fixation lever 3*h* is contained. Reference sign 26 denotes a switching gear supporting member that has a through-hole 26*h* in which one end portion of a switching gear shaft 52 is disposed to which a switching gear 51 is fixedly provided.

The switching gear supporting member 26 is fixedly provided in a predetermined position of the rotation mechanism main body 21, and turnably axially supports one end portion of the switching gear shaft 52 disposed in the through-hole 26*h*.

The motor portion 30 mainly has a motor case 31, a motor 32 serving as driving source indicated by a broken line, and a driving gear 33. The motor 32 is disposed in the motor case 31. The driving gear 33 is fixedly provided to a motor shaft 32*a* that protrudes from the motor 32.

The motor case 31 is fixedly provided to the motor attachment portion 22 in a predetermined state as illustrated in FIG. 4A.

The knob rotation portion 40 has a bending wheel 41, and the bending state display portion 17 as illustrated in FIG. 4A and FIG. 4B. The bending wheel 41 has a knob coupling portion 42 serving as a ring shaped member and an interlocking portion 43, in which the knob coupling portion 42 and the interlocking portion 43 are integrally fixed.

The interlocking portion 43 is a gear portion that has a gear 43g on an outer peripheral surface. A plurality of convex portions 44 are aligned in a circumferential direction in the knob coupling portion 42. The plurality of convex portions 44 are designed to be respectively contained in concave portions 3n located between a plurality of convex portions 3m of an irregularity portion (denoted by reference sign 3k in FIG. 2A) included in the second bending up and down knob 3g.

Since the convex portions 44 are respectively disposed in concave portions 3n, the second bending up and down knob 3g and the bending wheel 41 are integrated with each other. In the integrated state, the second bending up and down knob 3g rotates in a corresponding rotation direction along with the rotation of the bending wheel 41.

The bending state display portion 17 is a circular plate, and the rotation index 17m is provided in a predetermined position of a circular plate surface. Reference sign 45 denotes a coupling member, and one end portion of the coupling member 45 is integrally fixedly provided to a circular plate rear surface of the bending state display portion 17. The other end portion of the coupling member 45 is integrally fixedly provided in a predetermined position on an outer peripheral surface of the knob coupling portion 42 of the bending wheel 41.

Therefore, along with the clockwise or anticlockwise rotation of the bending wheel 41, the bending state display portion 17 rotates in the same direction. For this reason, a user can easily determine a bending angle (bending amount) of the second bending portion 2b2 by checking the location of the rotation index 17m.

Figure 4C:
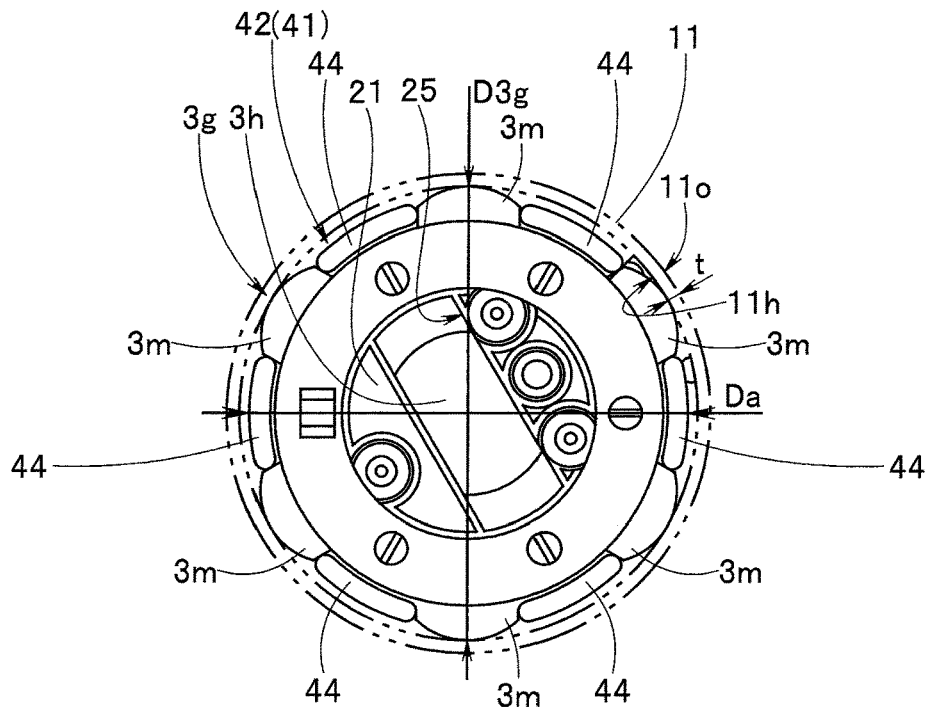
FIG. 4C is a drawing for describing an attached state where a convex portion of a knob connection portion is disposed in a concave portion of a second bending up and down knob in a predetermined state.

According to the present embodiment, an external diameter Da of the knob coupling portion 42 of the bending wheel 41 is set to be a smaller diameter than an external diameter D3g of the second bending up and down knob 3g as illustrated in FIG. 4C. The knob external diameter D3g of the second bending up and down knob 3g is previously set to be smaller than an outer circumference external diameter D3S to be arranged on an inner side relative to an outer peripheral surface (described as the outer circumference external diameter D3S) of the sub operation portion 3S as illustrated in FIG. 2A.

Therefore, in a state where the bending wheel 41 is integrated with the second bending up and down knob 3g, the outer peripheral surface of the bending wheel 41 is located on a more central side relative to an outer peripheral surface of the second bending up and down knob 3g.

Reference sign 11h denotes an inner peripheral surface of a knob rotation portion containing hole portion of the container case 11. An inner diameter of the inner peripheral surface 11h is previously set to be larger than the external diameter D3g of the second bending up and down knob 3g. In addition, a wall thickness t of the container case 11 is set such that an outer peripheral surface 11o of the knob rotation portion containing hole portion 11h and the outer peripheral surface of the sub operation portion 3S are flush with each other in the disposed state.

Note that the outer peripheral surface 11o of the knob rotation portion containing hole portion 11h may also be set to be slightly larger than the outer peripheral surface of the sub operation portion 3S.

In this manner, the outer peripheral surface of the bending wheel 41 is set to be arranged on the central side relative to the outer peripheral surface of the second bending up and down knob 3g. The wall thickness of the knob rotation portion containing hole portion 11h of the container case 11 is appropriately set, and a diameter of the outer peripheral surface 11o of the knob rotation portion containing hole portion 11h is set to be equal to or slightly larger than a diameter of the outer peripheral surface of the sub operation portion 3S.

As a result, in a state where a size of an outer shape of the container case 11 is reduced to cover the second bending up and down knob 3g to be disposed in the sub operation portion 3S, it is possible to suppress adverse effects, which is caused by the outer peripheral surface 11o of the knob rotation portion containing hole portion 11h of the container case 11 widely protruding from the outer peripheral surface of the sub operation portion 3S, on the operation of the first bending up and down knob 3c, the operation of the first bending left and right knob 3d, the operation of the first bending up and down fixation lever 3e, and the like.

Figure 4D:
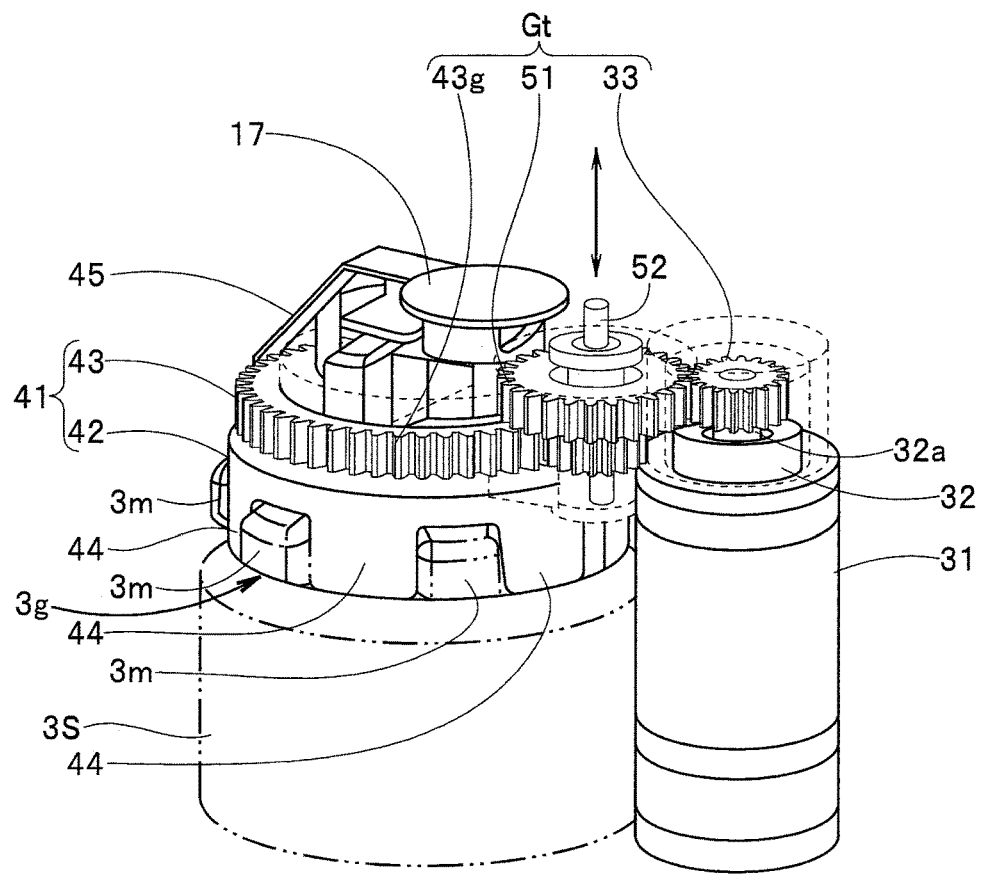
FIG. 4D is a drawing for describing a gear train constituted by a switching gear, a gear of an interlocking portion, and a driving gear fixedly provided to a motor shaft.

The transmission portion 50 mainly includes the switching gear 51 illustrated in FIG. 4B, the switching gear shaft 52, a cam ring 53, and the switching finger grip 16. As described above, the switching gear 51 is fixedly provided on one end portion side of the switching gear shaft 52. In the switching gear 51, the gear 43g of the interlocking portion 43 of the bending wheel 41 described above and the driving gear 33 fixedly provided to the motor shaft 32a constitute a gear train Gt as illustrated in FIG. 4D.

An engagement protrusion 52a protruding in a direction perpendicular to the shaft 52 is provided in the other end portion of the switching gear shaft 52 as illustrated in FIG. 4B. A cam groove 53a for ring is formed in the cam ring 53. A protrusion 53b for ring protrudes from an outer peripheral surface of the cam ring 53. The switching finger grip 16 includes a cylindrical portion 16a, and a cam groove 16b for cylinder is formed in the cylindrical portion 16a.

The outer peripheral surface side of the cam ring 53 is disposed on an inner peripheral surface side of the cylindrical portion 16a of the switching finger grip 16. In the disposed state, the protrusion 53b for ring is arranged in the cam groove 16b for cylinder. The engagement protrusion 52a is disposed on an inner peripheral surface side of the cam ring 53. In the disposed state, the engagement protrusion 52a is arranged in the cam groove 53a for ring.

In accordance with the configuration, the protrusion 53b for ring in the cam groove 16b for cylinder is moved along with the rotation of the switching finger grip 16, and the cam ring 53 is moved in an axis direction of the switching gear shaft 52. Along with the movement of the cam ring 53 in the axis direction, the engagement protrusion 52a in the cam groove 53a for ring is also moved in the axis direction.

As a result of these movements, along with the switching operation to the clockwise or anticlockwise rotation of the switching finger grip 16, as illustrated in FIG. 4D, the switching gear 51 of the gear train Gt is moved in the axis direction of the switching gear shaft 52 to switch to a state where the switching gear 51, a gear 43c of the interlocking portion 43, and the driving gear 33 are interlocked or a disconnected state.

In a transmitted state where the switching gear 51, the gear 43c of the interlocking portion 43, and the driving gear 33 are interlocked, rotation driving force of the motor 32 is transmitted to the bending wheel 41, and the second bending up and down knob 3g is rotated. In other words, when the switching gear 51, the gear 43c of the interlocking portion 43, and the driving gear 33 are set to be in the disconnected state, the driving force of the motor 32 is not transmitted to the bending wheel 41.

Figure 4E:
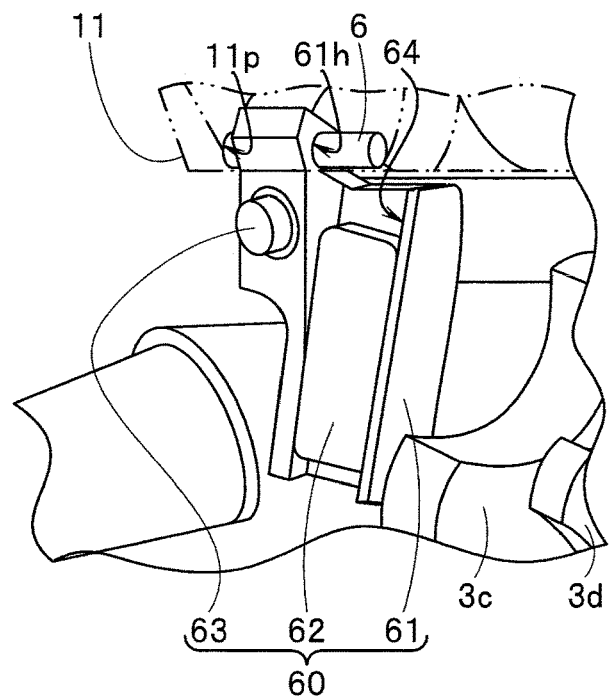
FIG. 4E is a drawing for describing attachment of an operation switch to the container case.

The operation switch 60 mainly includes the switch case 61 serving as a turning member, the operator 62 serving as an operation switch, and the dummy switch 63 serving as an operation member as illustrated in FIG. 4E. Note that an action of the dummy switch 63 will be described below.

An operator container portion 64 and a hinge pin hole 61h are provided in the switch case 61. Reference sign 6 denotes a hinge pin. The hinge pin 6 is arranged in a hinge hole 11p provided in the container case 11 and in the hinge pin hole 61h. As a result, the switch case 61 formed into a plate-like shape is turnably arranged with respect to the container case 11 about the hinge pin 6 that turnably supports one end.

Figure 5A:
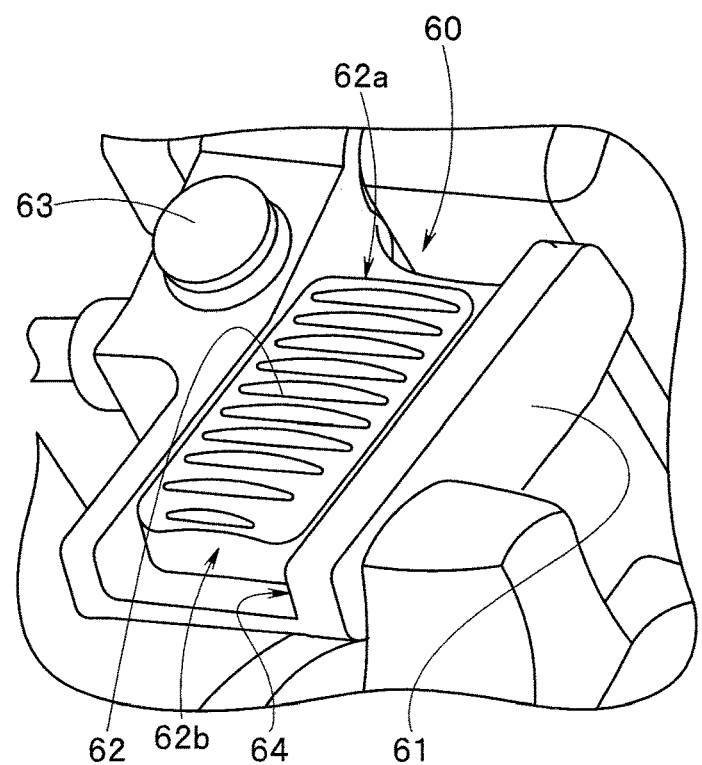
FIG. 5A is a drawing for describing a configuration of the operation switch.

As illustrated in FIG. 5A, the operator container portion 64 is an elongated groove, and the operator 62 is arranged to be slidable in a longitudinal direction. Therefore, in the configuration in FIG. 5A, the operator 62 functions as a so-called slide switch.

Figure 5B:
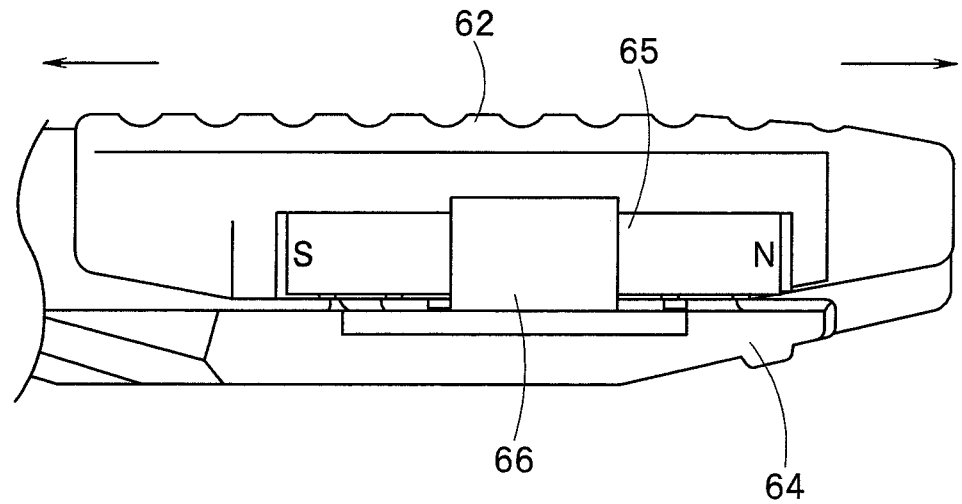
FIG. 5B is a drawing for describing a configuration example in which an operator is a slide switch.

As illustrated in FIG. 5B, a magnet 65 is disposed in a predetermined position of the operator 62, and a hall sensor (hereinafter, abbreviated as a sensor) 66 configured to detect a magnetic field of the magnet 65 is provided in the predetermined position in the operator container portion 64. The sensor 66 outputs a predetermined driving control signal to the motor in accordance with a change of a distance between the north pole and the south pole of the magnet 65.

Specifically, when a lower end 62b of the operator 62 illustrated in FIG. 5A is located in a lowermost part in a slide range of the operator container portion 64, the sensor 66 outputs a first driving control signal to the motor 32. As a result, the motor 32 is rotated and driven at a high speed, for example, and the second bending up and down knob 3g is rotated in the anticlockwise direction. On the other hand, when an upper end 62a of the operator 62 is located in an uppermost part in the slide range, the sensor 66 outputs a third driving control signal to the motor 32. As a result, the motor 32 is rotated and driven at a high speed, for example, and the second bending up and down knob 3g is rotated in the clockwise direction.

When the upper end 62a of the operator 62 is away from an intermediate part between the uppermost part and the lowermost part on an upper part side by a predetermined distance, the sensor 66 outputs a fourth driving control signal to the motor 32. The motor 32 is then rotated and driven at a low speed, for example, and the second bending up and down knob 3g is rotated in the clockwise direction. On the other hand, when the lower end 62b of the operator 62 is away from the intermediate part on a lower part side by a predetermined distance, the sensor 66 outputs a second driving control signal to the motor 32. The motor 32 is then rotated and driven at a low speed, for example, and the second bending up and down knob 3g is rotated in the anticlockwise direction.

Figure 5C:
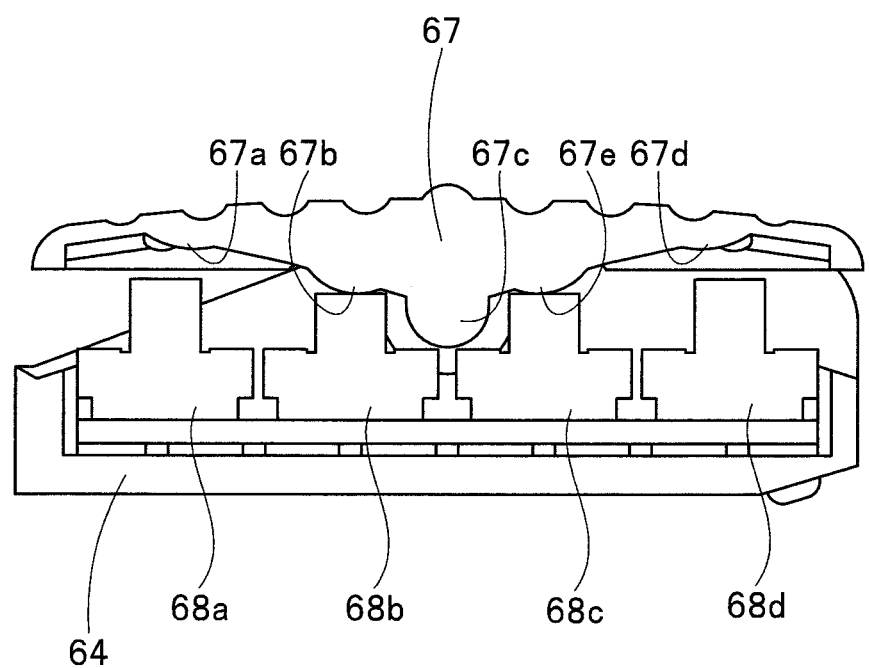
FIG. 5C is a drawing for describing a configuration example in which the operator is a seesaw switch.

Note that according to the aforementioned embodiment, the operator 62 is set as a slide switch. However, as illustrated in FIG. 5C, the operator may also be set as a seesaw switch 67 that rotates clockwise or anticlockwise by using a central convex portion 67c as a fulcrum.

Four switch convex portions 67a, 67b, 67d, and 67e are provided in the seesaw switch 67. A plurality, for example, four, of tactile switches 68a, 68b, 68c, and 68d are provided in the operator container portion 64.

When the seesaw switch 67 is in an initial state, the second tactile switch 68b and the third tactile switch 68c are in an on state, and the first tactile switch 68a and the fourth tactile switch 68d are in an off state. At this time, the motor 32 is in a stopped state.

Figure 5D:
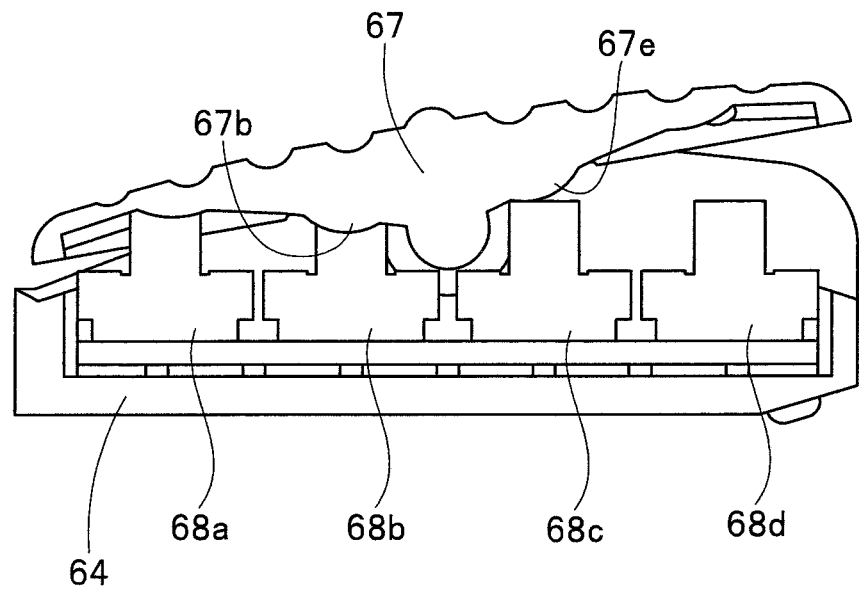
FIG. 5D is a drawing for describing an action example of the seesaw switch.

When the seesaw switch 67 is rotated anticlockwise, the third tactile switch 68c is switched from on to off as illustrated in FIG. 5D, and only the second tactile switch 68b is in the on state, the second driving control signal is outputted to the motor 32. The motor 32 is then driven at a low speed, and the second bending up and down knob 3g is rotated in the anticlockwise direction.

Figure 5E:
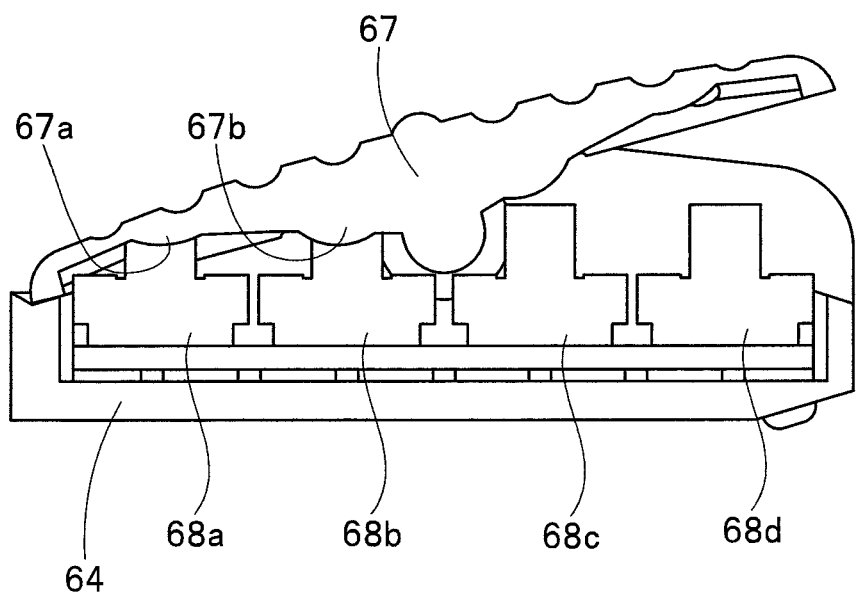
FIG. 5E is a drawing for describing another action example of the seesaw switch.

As illustrated in FIG. 5E, when the seesaw switch 67 is further rotated anticlockwise, the first tactile switch 68a is put into the on state in addition to the second tactile switch 68b. The first driving control signal is then outputted to the motor 32. The motor 32 is then driven at a high speed, and the second bending up and down knob 3g is rotated in the anticlockwise direction.

Note that although the illustration in the drawing is omitted, when the motor 32 is in the stopped state, and the seesaw switch 67 is rotated clockwise, the second tactile switch 68b is switched from on to off, only the third tactile switch 68c is put into the on state, and the fourth driving control signal is outputted to the motor 32. The motor 32 is then driven at a low speed, and the second bending up and down knob 3g is rotated in the clockwise direction.

Thereafter, when the seesaw switch 67 is further rotated clockwise, the fourth tactile switch 68d is put into the on state in addition to the third tactile switch 68c. The third driving control signal is then outputted to the motor 32. The motor 32 is then driven at a high speed, and the second bending up and down knob 3g is rotated in the clockwise direction.

In this manner, when the slide operation or the rotation operation of the operator 62 provided in the operation switch 60 is performed, the driving control signals are outputted to the motor 32, and the second bending up and down knob 3g is rotated and controlled by the driving force of the motor 32. As a result, the user can perform the bending operation of the second bending portion 2b2 without applying a large load to the finger.

Note that according to the aforementioned embodiment, the speed is set in two stages including the high speed and the low speed. However, the motor 32 may also be driven and controlled by changing the speed in one stage or three or more stages or stepwise on the basis of the detection result of the hall sensor 66. The number of tactile switches and the number of switch convex portions may be increased or decreased to change the speed in one stage or three or more stages.

Attachment to the sub operation portion 3S of the external mechanism 10 for endoscope will be described with reference to FIG. 6 to FIG. 7D.

First, when the container case 11 of the external mechanism 10 for endoscope is to be attached to the sub operation portion 3S, the user previously checks whether or not the second bending up and down fixation lever 3h provided in the second bending up and down knob 3g is in the free position.

Figure 6:
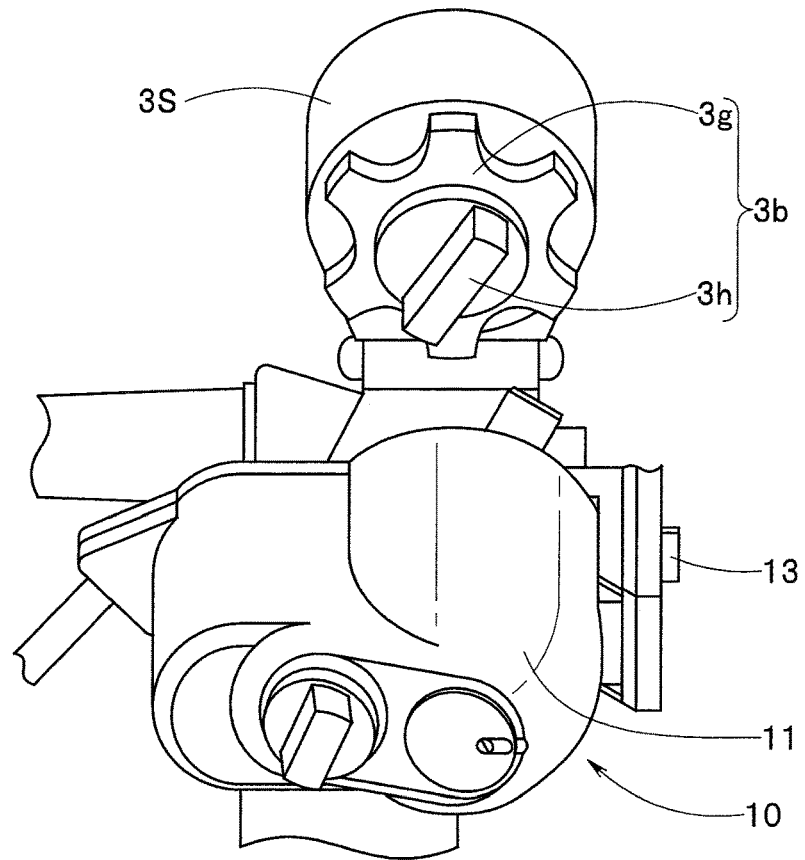
FIG. 6 is a drawing for describing a state where the container case of the external mechanism for endoscope is attached to the sub operation portion.

The user checks that the second bending up and down fixation lever 3h is arranged in the free position, and thereafter, as illustrated in FIG. 6, causes the container case 11 of the external mechanism 10 for endoscope to face the second bending up and down knob 3g provided in the sub operation portion 3S. At this time, the user causes the bending wheel 41 of the knob rotation portion 40 disposed in the case internal space to face the second bending up and down knob 3g.

Next, the user causes the container case 11 to approach the second bending up and down knob 3g. The user causes the concave portion for lever 25 provided in the rotation mechanism main body 21 to face the second bending up and down fixation lever 3h, and as illustrated in FIG. 4C described above, the second bending up and down fixation lever 3h is contained in the concave portion for lever 25. As a result, as illustrated in FIG. 2B described above, the container case 11 is arranged on the second bending up and down knob 3g.

In the container arrangement state, as illustrated in FIG. 4C described above, the convex portions 44 of the knob coupling portion 42 is disposed in the concave portion of the second bending up and down knob 3g in a predetermined state, and the second bending up and down knob 3g and the bending wheel 41 are integrated with each other.

The user sets the locking claw portion 15 of the hinge portion 14 to be engaged with and fixed to the locking portion 13 as illustrated in FIG. 2C and FIG. 2D described above. As a result, as illustrated in FIG. 7A, the attachment of the container case 11 to the sub operation portion 3S is completed.

In this manner, the concave portion for lever 25 that contains the lever 3h when the second bending up and down fixation lever 3h is located in the free position is provided in the rotation mechanism main body 21. According to this configuration, in a state where the external mechanism 10 for endoscope is mounted to the sub operation portion 3S, the second bending up and down knob 3g is reliably rotated in the clockwise direction or the anticlockwise direction along with the rotation of the knob coupling portion 42.

In other words, in a state where the second bending up and down fixation lever 3h is in the fixed position to restrict the turning, the external mechanism 10 for endoscope is not to be mounted to the sub operation portion 3S. Therefore, it is possible to previously avoid a failure which may be caused when the second bending up and down knob 3g where the turning is restricted is rotated by the driving force of the motor 32.

Figure 7A:
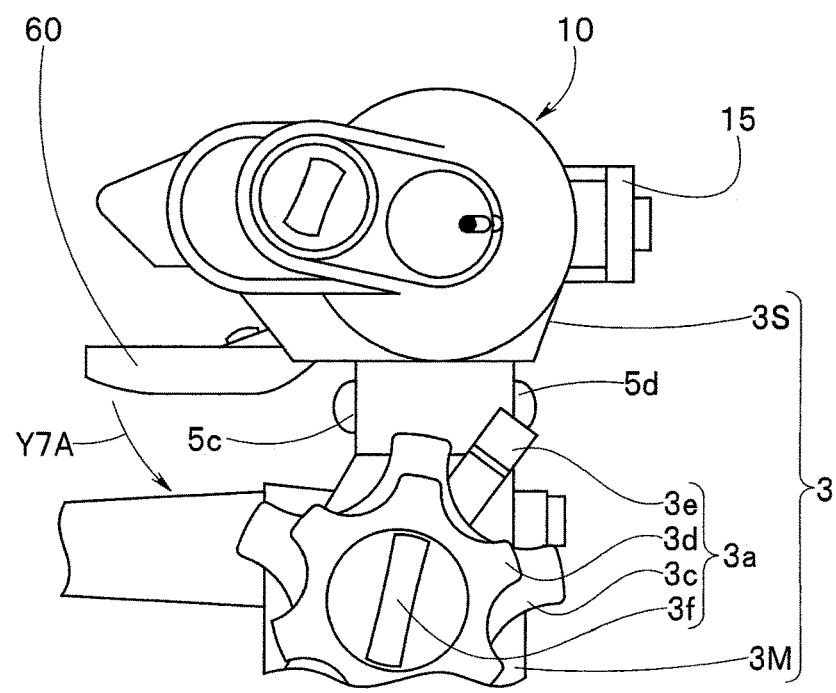
FIG. 7A is a drawing for describing a state where the attachment of the container case to the sub operation portion is completed and an initial position of the operation switch in the completed state.
Figure 7B:
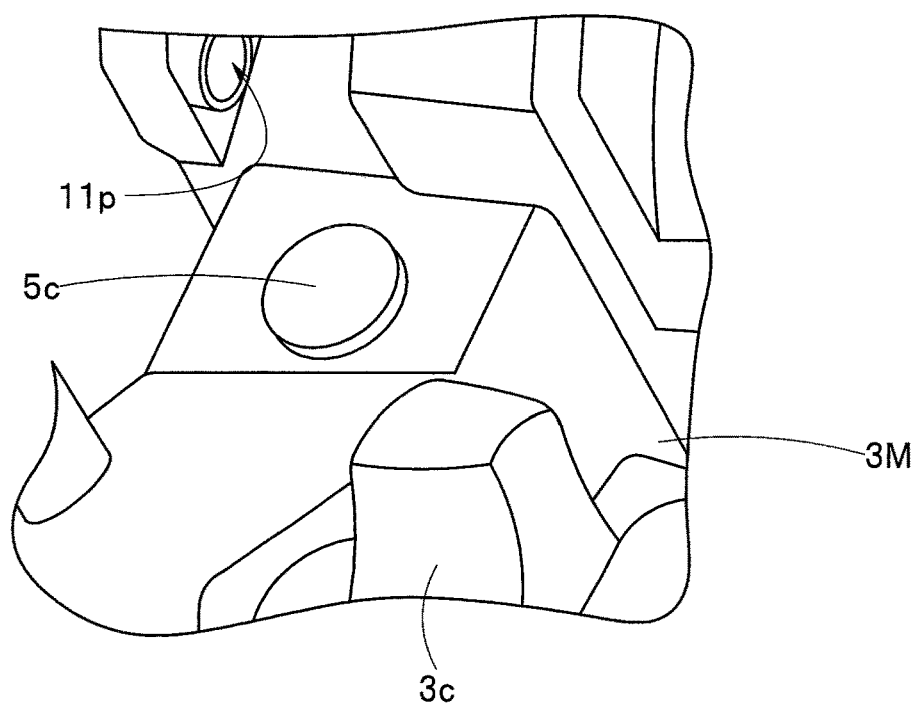
FIG. 7B is a drawing for describing exposure of a remote switch in the attachment completed state.

In a state where the container case 11 is attached to the sub operation portion 3S as illustrated in FIG. 7A and FIG. 7B, the remote switch 5c is exposed when the operation switch 60 is arranged in the initial position.

After the container case 11 is attached to the sub operation portion 3S, as illustrated in FIG. 7A, the user pushes down the switch case 61 of the operation switch 60 that can be turned with respect to the container case 11 in an arrow Y7A direction.

Figure 7C:
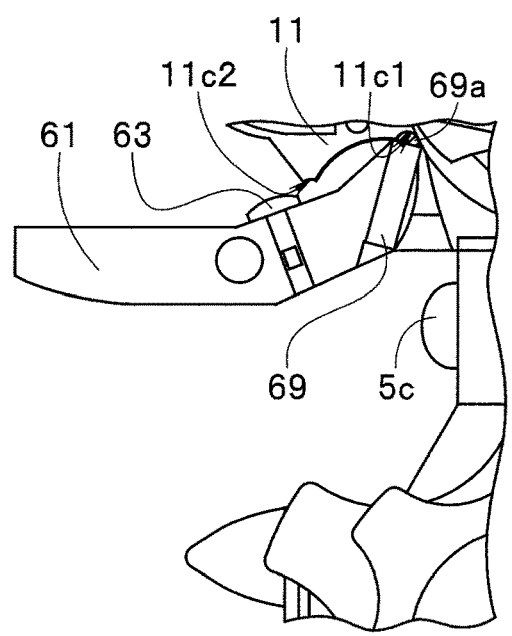
FIG. 7C is a drawing for describing a first engagement state where a slide convex portion of a ball spring plunger is arranged in a first concave portion of the container case.

A first engagement state where a slide convex portion 69a of a ball spring plunger 69 provided in the switch case 61 and a first concave portion 11c1 of the container case 11 is then released as illustrated in FIG. 7C, and the switch case 61 moves towards between one surface of the main operation portion 3M illustrated in FIG. 7B and one end surface of the first bending up and down knob 3c.

Figure 7D:
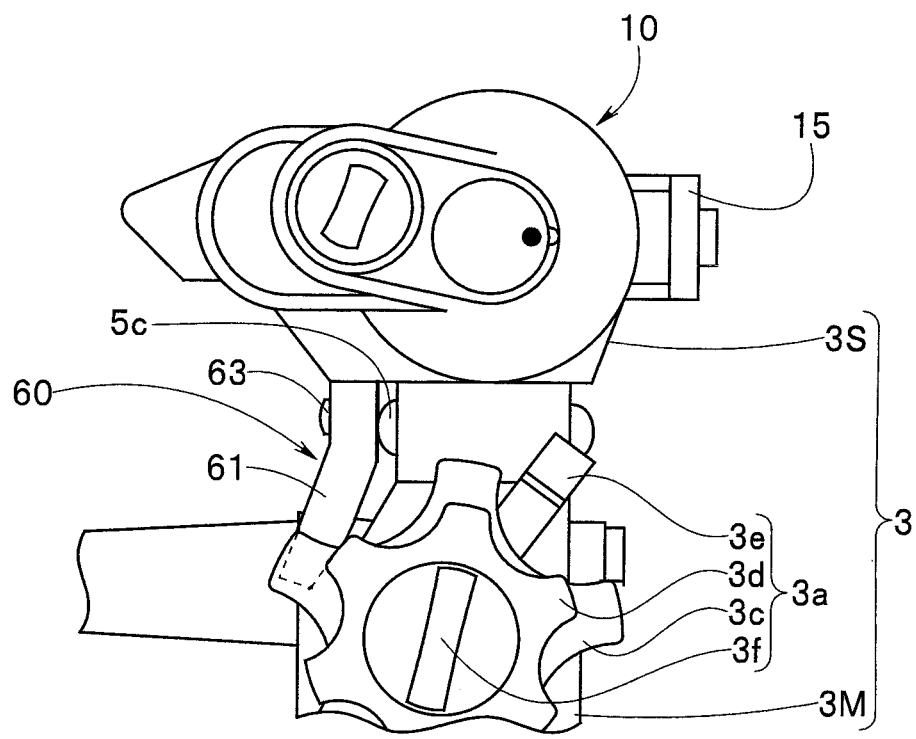
FIG. 7D is a drawing for describing a mechanism attached state where the operation switch of the external mechanism for endoscope is disposed to be adjacent to a first bending operation apparatus provided in a main operation portion.

Thereafter, the slide convex portion 69a of the ball spring plunger 69 is engaged with a second concave portion 11c2 of the container case 11 to establish a second engagement state and complete the movement of the operation switch 60 as illustrated in FIG. 7D, and the operation switch 60 of the external mechanism 10 for endoscope is disposed in a first position adjacent to the first bending operation apparatus 3a provided in the main operation portion 3M.

As a result, the exposed remote switch 5c is covered with the switch case 61. At this time, the dummy switch 63 on a remote switch side is arranged on the remote switch 5c. In this state, the switch operation of the remote switch 5c can be performed by a pressing operation to move the dummy switch 63 in a thickness direction of the switch case 61.

The action of the endoscope 1 will be described in which the external mechanism 10 for endoscope is attached to the sub operation portion 3S, and the operation switch 60 is disposed to be adjacent to the first bending operation apparatus 3a.

When an endoscope inspection is performed by using the endoscope 1 in which the external mechanism 10 for endoscope is attached to the sub operation portion 3S, the user grasps the main operation portion 3M. The user grasps the insertion portion 2 by a hand different from the hand that grasps the main operation portion 3M, and inserts the insertion portion 2 into a body via a mouth cavity, for example.

At this time, the user appropriately performs the bending operation of the first bending portion 2b1 and the second bending portion 2b2. In other words, the user appropriately performs the turning operation of the first bending up and down knob 3c or the first bending left and right knob 3d of the first bending operation apparatus 3a provided in the main operation portion 3M to cause the first bending portion 2b1 to perform the bending operation in the up and down direction, the left and right direction, or the like, and also appropriately operates the operator 62 of the operation switch 60 adjacent to the first bending operation apparatus 3a of the main operation portion 3M to cause the second bending portion 2b2 to perform the bending operation in the up and down direction.

In this manner, the switch case 61 of the operation switch 60 is provided between a first position and a second position further away from the first position to be able to turn with respect to the container case 11 of the external mechanism 10 for endoscope. The ball spring plunger 69 is provided in the switch case 61, and also the first concave portion 11c1 and the second concave portion 11c2 are provided on the container case 11 side.

As a result of these provisions, in the second position corresponding to the first engagement state where the slide convex portion 69a of the switch case 61 is arranged in the first concave portion 11c1, the attachment can be smoothly performed without disturbing the attachment by the operation switch 60 when the external mechanism 10 for endoscope is attached to the sub operation portion 3S.

After the external mechanism 10 for endoscope is attached to the sub operation portion 3S, the engagement state of the ball spring plunger 69 is switched from the first engagement state to the second engagement state. According to this configuration, the operation switch 60 is disposed to be adjacent to the first bending operation apparatus 3a of the main operation portion 3M, and the turning operation of the first bending up and down knob 3c and the first bending left and right knob 3d of the first bending operation apparatus 3a, the slide operation of the operator 62 of the operation switch 60, and the like can be performed by the finger of the hand of the user that grasps the main operation portion 3M.

The user can more smoothly perform the insertion of the insertion portion 2 into a deep part inside the body by slightly moving the finger of the hand to appropriately perform the bending operation of the first bending portion 2b1 and the second bending portion 2b2 provided in the bending portion 2b without touching the remote switch.

Figure 8:
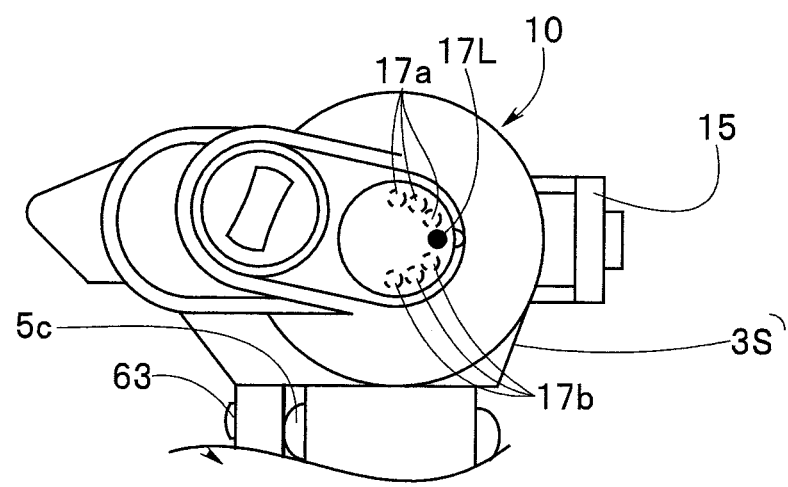
FIG. 8 is a drawing for describing another configuration example of a bending state display portion.

According to the aforementioned embodiment, the rotation index 17m is provided in the bending state display portion 17 to check the bending angle. However, the rotation index may also be an LED lamp 17L illustrated in FIG. 8. A flashing interval of the LED lamp 17L is shortened as the bending amount is increased. A lighting state is established when a maximum bending state is approached. Note that the bending direction is determined on the basis of the operation direction of the operator 62.

According to the aforementioned embodiment, the rotation index 17m is set as the single LED lamp 17L. However, the LED lamp 17L is set as a reference, and a plurality of LED lamps 17a and 17b may also be aligned in the surrounding. In accordance with this configuration, it is possible to check that the bending amount of the bending portion 2b2 is increased as the number of lightings of the LED lamps is increased.

Note that in the aforementioned explanation, the external mechanism 10 for endoscope is mounted to the sub operation portion 3S, and the bending operation of the second bending portion 2b2 is performed without applying a large load to the finger of the user. However, the knob to which the external mechanism 10 for endoscope is mounted is not limited to the second bending up and down knob 3g provided in the sub operation portion 3S, and may also be the first bending left and right knob 3d provided in the main operation portion 3M or both the first bending up and down knob 3c and the first bending left and right knob 3d.

Note that the present invention is not limited only to the embodiment described above, but various modifications can be made in a scope without departing from the gist of the invention.

According to the present invention, the external mechanism for endoscope can be realized where it is easy to perform the attachment to and detachment from the operation portion, and the operability of the endoscope and the layout are not affected in the attached state.

What is claimed is:

1. An external mechanism for an endoscope, comprising:
a wheel configured to be engaged with an operation knob of a bending operation apparatus provided in an operation portion of the endoscope;
a motor configured to generate a driving force for rotating the wheel;
an operation switch configured to output a driving control signal for the motor;
a container case that contains the wheel and the motor;
a clamp with which the container case can be attached to and detached from the operation portion;
a switch case turnably attached to the container case, and configured to be able to turn between a first position that covers a part of the operation portion of the endoscope and a second position further away from the operation portion of the endoscope than the first position; and
a dummy switch provided in the switch case, the dummy switch being configured to operate an endoscope-side switch via the switch case when the switch case is in the first position, the endoscope-side switch being arranged in a part of the operation portion of the endoscope.

2. The external mechanism for endoscope according to claim 1, wherein the switch case is formed into a plate shape with one end turnably supported, and the endoscope-side switch is operated when the dummy switch is operated to be moved in a thickness direction of the switch case.

3. The external mechanism for endoscope according to claim 2, wherein the dummy switch operates the endoscope-side switch by moving the dummy switch in the thickness direction.

4. An endoscope system comprising:
an endoscope; and
an external mechanism that can be attached to and detached from an operation portion of the endoscope, wherein
the endoscope comprises:
a bending knob provided in the operation portion and configured to bend a bending portion of an insertion portion when the bending knob is turned; and
an endoscope operation control switch arranged in a part of the operation portion and configured to execute a predetermined operation in the endoscope by being operated, and
the external mechanism includes
a wheel configured to be engaged with the bending knob to turn the bending knob,
a motor configured to generate a driving force for rotating the wheel,
an operation switch configured to output a driving control signal for the motor,
a container case that contains the wheel and the motor,
a clamp with which the container case can be attached to and detached from the operation portion,
a switch case turnably attached to the container case, and configured to be able to turn between a first position that covers a part of the operation portion of the endoscope and a second position away from the first position; and
a dummy switch provided in the switch case, the dummy switch being configured to operate the endoscope operation control switch via the switch case when the switch case is in the first position.

* * * * *